US010251587B2

(12) United States Patent
Kahlman et al.

(10) Patent No.: US 10,251,587 B2
(45) Date of Patent: Apr. 9, 2019

(54) CONDITIONING OF CHEMO-OPTICAL SENSORS FOR TRANSCUTANEOUS APPLICATION

(71) Applicant: KONINKLIJKE PHILIPS N.V., Eindhoven (NL)

(72) Inventors: Josephus Arnoldus Henricus Maria Kahlman, Tilburg (NL); Hans Willem Van Kesteren, Eindhoven (NL); Nicolaas Lambert, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 629 days.

(21) Appl. No.: 14/895,937

(22) PCT Filed: Jun. 6, 2014

(86) PCT No.: PCT/EP2014/061770
§ 371 (c)(1),
(2) Date: Dec. 4, 2015

(87) PCT Pub. No.: WO2014/195438
PCT Pub. Date: Dec. 11, 2014

(65) Prior Publication Data
US 2016/0135723 A1 May 19, 2016

(30) Foreign Application Priority Data
Jun. 6, 2013 (EP) .................................... 13170723

(51) Int. Cl.
*A61B 5/1455* (2006.01)
*A61B 5/145* (2006.01)
*G01N 33/00* (2006.01)

(52) U.S. Cl.
CPC ...... *A61B 5/14552* (2013.01); *A61B 5/14542* (2013.01); *A61B 5/14551* (2013.01); *G01N 33/004* (2013.01)

(58) Field of Classification Search
CPC ... A61B 5/145; A61B 5/1455; A61B 5/14539; A61B 5/14556; A61B 5/1477;
(Continued)

(56) References Cited

U.S. PATENT DOCUMENTS 3,754,867 A    8/1973  Guenther
4,041,932 A *  8/1977  Fostick .............. A61B 5/14539
                                                356/39

(Continued)

FOREIGN PATENT DOCUMENTS

DE     102005033926 A1    1/2007
EP         1192938 A2     4/2002
(Continued)

OTHER PUBLICATIONS

Oroszi, L. et al., "Control of electro-osmostic flow by light", Applied Physics Letters, 89, Institute of Biophysics, Biological Research Centre, Hungarian Academy of Sciences, Jul. 2006.
(Continued)

*Primary Examiner* — Eric Winakur
*Assistant Examiner* — Chu Chuan (J J) Liu
(74) *Attorney, Agent, or Firm* — Michael W. Haas

(57) ABSTRACT

The present invention relates to a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is
(Continued)

adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas. The present invention also relates to a system comprising such a chemo-optical sensor, as well as to a method for conditioning a chemo-optical sensor unit for measuring a concentration of a gas and a thereby obtainable conditioned sensor.

16 Claims, 4 Drawing Sheets

(58) Field of Classification Search
CPC .............. A61B 5/0059; A61B 5/14551; A61B 5/14552; A61B 5/14542
See application file for complete search history.

(56) References Cited

U.S. PATENT DOCUMENTS

| | | |
|---|---|---|
| 4,488,557 A | 12/1984 | Engel |
| 5,114,676 A | 5/1992 | Leiner et al. |
| 6,602,716 B1 | 8/2003 | Klimant |
| 2001/0034479 A1* | 10/2001 | Ring .................. A61B 5/14556 600/322 |
| 2003/0003593 A1 | 1/2003 | Wallach |
| 2005/0176084 A1 | 8/2005 | Burkoth |
| 2009/0004751 A1 | 1/2009 | Leiner et al. |

FOREIGN PATENT DOCUMENTS

| | | |
|---|---|---|
| EP | 1965198 A1 | 9/2008 |
| JP | 2005513428 A | 5/2005 |
| JP | 2008279237 A | 11/2008 |
| WO | 02056023 A1 | 7/2002 |
| WO | 2013064313 A1 | 5/2013 |

OTHER PUBLICATIONS

Kocincova, "New pH Sensitive Sensor Materials. Luminescent Fiber-Optic Dual Sensors for Non-Invasive and Simultandous Measurement of pH and pO2 (Dissolved Oxygen) in Biological Systems", PhD Thesis, University of Regensburg, 2007, Pages.

Schaferling, "The Art of Fluorescence Imaging With Chemical Sensors" Chemical Sensors, Angewandte Chemie International Edition, 51(15), 2012, pp. 3532-3554.

Anonymous, "CO2 Sensors", Presens, XP-002715621, Retrieved From the Interneta; URL:http://www.presens.de/products/brochures/category/sensor-probes/brochure/co2-sensors.html, Oct. 28, 2013, pp. 1-5.

Mills et al, "Fluorescent Carbon Dioxide Indicators", University of Strathclyde, XP055085367, 2005, pp. 1-43.

* cited by examiner

CONDITIONING OF CHEMO-OPTICAL SENSORS FOR TRANSCUTANEOUS APPLICATION

CROSS-REFERENCE TO PRIOR APPLICATIONS

This application is the U.S. National Phase application under 35 U.S.C. § 371 of International Application Serial No. PCT/EP2014/061770, filed on Jun. 6, 2014, which claims the benefit of European Application. 13170723.4, filed on Jun. 6, 2013. These applications are hereby incorporated by reference herein.

FIELD OF THE INVENTION

The present invention relates to a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas. The present invention also relates to a system comprising such a chemo-optical sensor, as well as to a method for conditioning a chemo-optical sensor unit for measuring a concentration of a gas and a thereby obtainable conditioned sensor.

BACKGROUND OF THE INVENTION

Neuromuscular disease, chronic obstructive pulmonary disease (COPD) and obese hypoventilation patients often suffer from chronic respiratory failure. Said patients need regular treatment of their respiratory failure at home. Hypoxemic patients are treated by oxygen therapy (mostly without ventilator support), while treatment by Invasive Ventilation (IV) and Non Invasive Ventilation (NIV) with environmental air helps bringing the high carbon dioxide ($CO_2$) blood gas level of hypercapnic patients back to an acceptable level. The efficacy of the ventilation is checked by measuring the base-line and the trends in the arterial oxygen and carbon dioxide levels during nocturnal NIV.

Arterial blood gas measurements form the golden standard. Before starting ventilation treatment at home, patients stay at the hospital to optimize ventilator settings and monitor arterial blood gas values. Depending on disease severity and stability, patients have to return more or less regularly to the hospital for checks. A respiratory nurse can also visit the patient at home to check the ventilator and to install equipment that enables non-invasive monitoring of blood gas partial pressures. At home, blood gas levels are monitored typically during a night and data are stored together with ventilator and respiratory data for later analysis at the hospital.

The state of the art in non-invasive blood oxygenation monitoring, is by measuring the arterial oxygen saturation, which relates to the partial oxygen pressure via the oxygen dissociation curve. Pulse oximetry ($SpO_2$) is an optical method for non-invasive monitoring of arterial oxygen saturation in a patient and has become one of the most commonly used technologies in clinical practice. Pulse oximetry is a reasonably low cost technology and is easy to use. It is the preferred method for blood oxygenation monitoring at home.

The state of the art in non-invasive monitoring of the partial pressure of $CO_2$ is by means of capnography or by transcutaneous $CO_2$ ($PtcCO_2$) monitoring. For intubated patients with a healthy lung the end tidal $CO_2$ ($etCO_2$) value obtained by capnography offers a good indication of the arterial $CO_2$ value. However, in case of non-invasive ventilation where air leaks between mask and face are usually present and the patients have severe respiratory diseases capnography is often not a reliable method. In most hospitals a combination is used of capnography for trend monitoring and analysis of an arterial blood sample to obtain an occasional accurate value.

Transcutaneous $CO_2$ monitoring is not disrupted by air-leaks and respiratory diseases but requires trained personal to obtain reliable values and shows some inaccuracy due to variation in skin properties among adults. At home $CO_2$ blood gas monitoring is less frequently used than oximetry despite its high relevance for patients receiving ventilation.

Current transcutaneous $CO_2$ sensors are all based on a 40 year old concept of (i) a thermostatically controlled heater to increase blood perfusion and gas-permeability of the skin; (ii) a fluid layer between skin and sensor membrane; (iii) a gas-permeable membrane covering the sensor; (iv) an electrolyte solution between membrane and sensor; (v) a sensor comprising an electrochemical pH sensor and reference electrode; and (v) an algorithm to compensate for temperature effects and skin metabolism.

EP 1 965 198 A1 describes a device for determining $CO_2$ in gaseous or liquid samples comprising a polymer matrix and an indicator embedded in the polymer matrix, wherein the indicator comprises a pH sensitive dye and a metal cation complex, wherein an anion of the pH-sensitive dye and the metal cation form a salt which is soluble in the polymer matrix.

Mills and Hodgen, 2005, Advanced concepts in fluorescence sensing, Topics in Fluorescence Septroscopy, 9(9), pages 119 to 162 discloses several features of wet carbon dioxide optical sensors systems and dry carbon dioxide optical sensors systems, in particular information on suitable dyes and luminescent indicators.

A further example of a prior art chemo-optical sensor for transcutaneous application is depicted in FIG. 1, wherein on top of an optical transparent carrier material two layers of 'silicon rubber-like' gas-permeable materials are deposited The first layer—the sensing layer—comprises a mixture of two luminescent dyes in a lipophilic phase transfer agent within a hydrophobic polymer, namely a reference dye having a long luminescent life-time and a pH-sensitive indicator dye having a short luminescent life-time. A second membrane layer comprises light reflecting material ($TiO_2$) particles and prevents ion transport to and from the sensing layer. $CO_2$ gas typically diffuses through said membrane into the first (sensing) layer and changes the pH, which in turn modifies the luminescence from the indicator dye. By using a dual life-time referencing technique, which effectively measures the time response of modulated light excitation, the percentage of $CO_2$ gas can be calculated.

The lipophilic phase transfer agent also serves as chemical buffer material to provide water for the production of carbonic acid. However, osmotic imbalance at the site of application of the sensor, e.g. in a contact zone with a contact medium, may initiate molecular perturbations such as water transport in the sensor or out of the sensor, which may lead to unwanted sensitivity changes of the sensor, thus requiring a calibration or re-calibration of the sensor.

In consequence, there is a need for the development of an improved chemo-optical sensor for transcutaneous applications, in which no sensitivity changes due to molecular perturbations occur.

OBJECTS AND SUMMARY OF THE INVENTION

The present invention addresses these needs and provides means and methods for effectively measuring the concentration of gas, in particular of $CO_2$ in an osmotically unbalanced environment such as the skin. The above objective is in particular accomplished by a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas. In particular, it was surprisingly found by the inventors that a conditioning of such a chemo-optical sensor unit, prior to the application of the sensor on the skin, with an organic compound, e.g. a polyhydroxy alkane such as propylene glycol, molecular disturbances such as water transport out of the chemo-optical sensor unit and between the chemo-optical sensor unit and a contact medium are strongly diminished such that no sensitivity changes during gas measurement, e.g. during the measurement of $CO_2$, occur. Thus, when the chemo-optical sensor unit according to the present invention is attached to a person's skin via a contact medium that is arranged between the at least one gas permeable layer and the skin, gasses present in the skin, for instance $O_2$ or $CO_2$, pass the gas permeable layer into a sensing layer as long as the gas partial pressure in the skin is higher than the gas partial pressure in the chemo-optical sensor unit. Due to presence of the organic compound, e.g. a polyhydroxy alkane such as propylene glycol, in the chemo-optical sensor unit and in the contact medium an osmotically equilibrated environment may be provided which allows for the effective detection of the concentration of $O_2$ or $CO_2$ without the need for any additional calibration steps and without fearing a progressive falsification or invalidity of the measured values due to an influence of water influx to the sensing layer.

In a preferred embodiment of the present invention the at least one gas-permeable layer and/or said at least one sensing layer of the chemo-optical sensor unit comprises the first compound other than water.

In a further preferred embodiment the contact medium is gas-permeable, biocompatible and capable of at least partially penetrating said chemo-optical sensor unit. In an optional embodiment, the contact medium is further also thermally conductive. In yet another preferred embodiment the first compound other than water is an organic compound such as a carbohydrate, a reduced carbohydrate, a polysaccharide, a polyhydroxy alkane, or any derivative thereof. In a further preferred embodiment, the first compound other than water is a $C_2$-$C_{10}$ alcohol, or a derivative thereof.

In another preferred embodiment of the present invention, the first compound other than water is propylene glycol, xylitol, sorbitol or glycerol, or a derivative thereof.

In yet another preferred embodiment of the present invention, said contact medium additionally comprises (i) water and (ii) dissolved sodium chloride.

In a further embodiment of the present invention said chemo-optical sensor is provided in a conditioning fluid comprising said first compound as defined herein above. In a specifically preferred embodiment of the present invention said conditioning fluid is identical to the contact medium as defined herein above.

In a further preferred embodiment, said at least one gas-permeable layer and/or said at least one sensing layer comprises a silicon rubber.

In another preferred embodiment, the first compound other than water is present in said chemo-optical sensor unit in such a concentration that the optical response is stable when the chemo-optical sensor is in contact with said contact medium having a constant gas concentration.

In an additional embodiment of the present invention, which is also preferred, the sensing layer comprises luminescent material and the gas-permeable layer is adapted to prevent light from passing through the gas-permeable layer.

In a further preferred embodiment of the present invention the chemo-optical sensor unit is a transcutaneous sensor unit for measuring blood gas concentration. It is particularly preferred that the chemo-optical sensor unit is for measuring the blood gas concentrations of $O_2$ and/or $CO_2$. In a more preferred embodiment, the chemo-optical sensor unit is for measuring the blood gas concentration of $CO_2$.

In a further embodiment the chemo-optical sensor unit as defined herein above further comprises: at least one light source adapted to irradiate the sensing layer, and optionally a light guiding structure connected to the light source; and at least one detection device adapted to detect the optical response of the sensing layer, and optionally a light guiding structure connected to the detection device. In a preferred embodiment, at least one of the light source, light guiding structure and/or the detection device are detachably connected to the chemo-optical sensor unit.

In a further aspect, the present invention relates to a system for patient monitoring and/or ventilation of a patient, comprising a chemo-optical sensor unit as defined herein above, a ventilation device and/or a monitoring device.

In yet another aspect the present invention relates to a method for conditioning a chemo-optical sensor unit for transcutaneous measurement of a concentration of a gas, comprising at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas; the method comprising contacting said chemo-optical sensor unit with a conditioning fluid, preferably with a conditioning fluid comprising a first compound other than water as defined in herein above, or with a contact medium as defined herein above.

In a preferred embodiment said contacting step is performed until said first compound has reached an equilibrium in said gas-permeable layer and/or said sensing layer.

In a further aspect the present invention relates to a conditioned chemo-optical sensor unit for transcutaneous measurement of a concentration of a gas obtainable by the method for conditioning a chemo-optical sensor unit for transcutaneous measurement of a concentration of a gas as defined herein above.

DETAILED DESCRIPTION OF THE EMBODIMENTS

Figure 1:
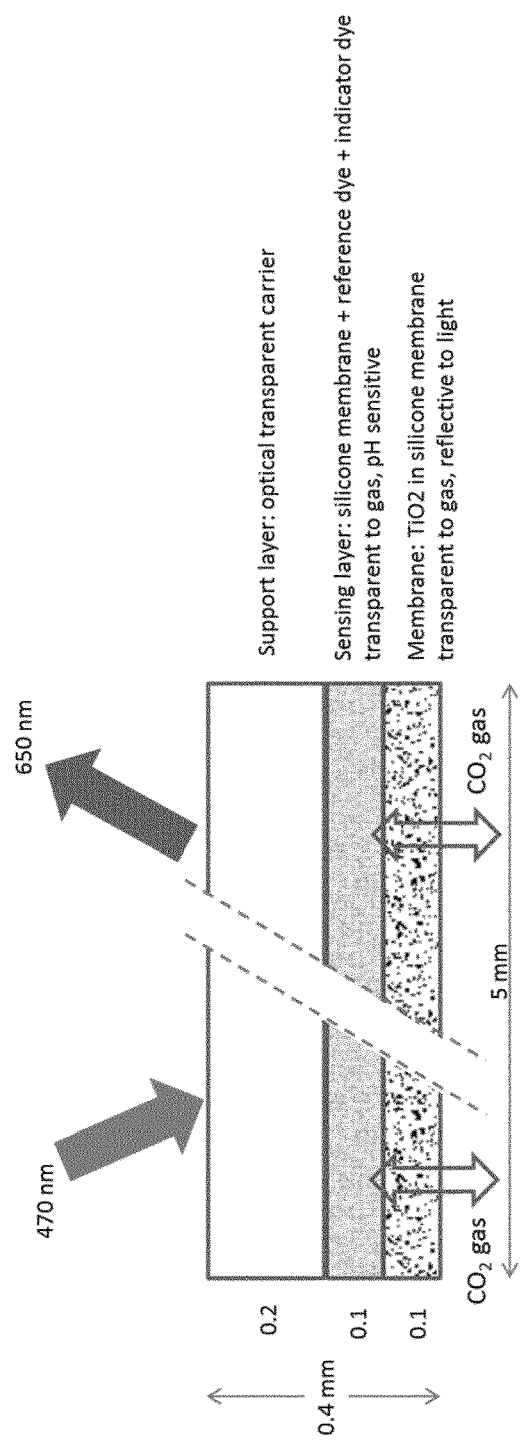
FIG. 1 shows the principles of a chemo-optical sensor for transcutaneous application. The figure depicts a chemo-optical sensor comprising a support layer with an optical transparent carrier, a sensing layer comprising a silicone membrane, a reference dye and an indicator dye, which is transparent to gas and pH sensitive, as well as a layer comprising $TiO_2$ in a silicone membrane, which is transparent to gas and reflective to light. The chemo-optical sensor may, for example, be excited at 470 nm (blue-green LED) and the luminescence may be detected from indicator and reference dyes in the range of 500 to 700 nm (red). The reference dye has a slow response and the luminiphores may, for example, be packed in spheres to protect them from $O_2$. The indicator dye has a fast response and it is primary sensitive to $H^+$ (pH), leading to an decrease of the amplitude and a yellow coloring under white light illumination due to pH decrease caused by $CO_2$ increase. The frequency of the illumination light intensity modulation is chosen such that a phase shift at about 45° is obtained.

The present invention relates to a chemo-optical sensor unit for transcutaneous measurement of a concentration of a gas.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a chemo-optical sensor unit for transcutaneous measurement of a concentration of a gas, comprising: at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas.

The term "concentration of a gas" relates to the amount of gas arriving at the chemo-optical sensor due to diffusion from zones or sectors to be measured. A "gas" may be any gaseous material. It is preferred that the gas is a biologically produced or biologically active or relevant gas. Examples of such gases are $O_2$, $CO_2$, CO, $N_2$, $NH_3$, NO, $H_2S$. It is preferred that the gas whose concentration should be measured is $O_2$ and/or $CO_2$. It is particularly preferred that the gas whose concentration should be measured is $CO_2$.

The term "sensing layer" as used herein refers to a layer which may be irradiated or excited and which may subsequently generate a light of a different wavelength due to the excitation of an optically reactive material, e.g. luminescence such as fluorescence, as optical response, wherein the intensity of the generated light depends on the concentration of gas molecules present in or dissolved in the sensing layer. The measurement of the optical response, e.g. luminescence such as fluorescence, of a certain intensity and wavelength, allows to calculate the gas concentration in the sensing layer, e.g. being diffusing or having diffused into the sensing layer from deeper layers such as the skin. This measurement may further allow a calculation of the concentration of such gas in the sector to be measured, e.g. in the sector of the skin on which the chemo-optical sensor is placed.

The sensing layer may be composed of filler material which is passable for gas molecules. An example of such filler material is silicone rubber material. In a preferred embodiment, the sensing layer may thus comprise silicone rubber or essentially consist of silicon rubber material. The sensing layer may further comprise compounds such as water or chemical buffers. The sensing layer may accordingly be buffered at a specific pH or comprise a certain amount of protons and/or hydroxide ions, e.g. have a certain pH. The pH which may be changed due to the diffusion of gases, in particular $CO_2$ into the sensing layer. Preferably, $CO_2$ may diffuse into the sensing layer and change the pH in said sending layer by interacting with water, thus increasing the concentration of protons and thus changing the pH.

The term "irradiated with a predetermined radiation" as used herein means that the sensing layer may be irradiated or excited with radiation of a suitable wavelength, in particular a wavelength which is able to generate an optical response of the sensing layer. For example, the irradiation may be carried out with visible light, infrared light and/or ultraviolet light. Preferred examples of a predetermined radiation is light of the green-blue visible spectrum, e.g. of a wavelength of about 400 to 500 nm, e.g. 440 nm, 450 nm, 460 nm, 470 nm, 480 nm, 490 nm etc. The radiation, i.e. the light wavelength as well its intensity, may in general be made dependent on or be adapted to the optically reactive material in the sensing layer. For specific optically reactive material suitable corresponding excitation wavelengths may be used.

Within the context of the chemo-optical sensor unit the sensing layer is adapted to measure an optical response of the at least one sensing layer, whose optical response depends on the concentration of the gas.

In a preferred embodiment, the sensing layer comprises as optically reactive material a luminescent material. The "luminescent material" may comprise one or more than one dye. The dye may be sensitive for the gas to be measured, e.g. for $CO_2$. The sensitivity may be indirect, for example, be provided via a sensitivity to pH, which in turn is influenced by gas, e.g. $CO_2$, that is diffusing into the sensing layer. Alternatively, the gas may itself have a direct influence on the sensitivity of the dye. In a particularly preferred embodiment, the luminescent material comprises two dyes. For example, the luminescent material may comprise a gas-sensitive dye which works as indicator dye, and a gas-insensitive dye which works as reference dye. In further embodiments, the two dyes as mentioned above may have different decay times. For example, the gas-sensitive dye may have a fast luminescence decay time, whereas the gas-insensitive dye may have a slow luminescence decay time. Examples of suitable reference dyes which are inert to a gas and which show a long decay time include: (1) transition metal complexes with ruthenium(II), rhenium (I), or osmium and iridium as central atom and diimine ligands; (2) phosphorescent porphyrins with platinum, palladium, lutetium or tin as central atom; (3) phosphorescent complexes of rare earths, for instance europium, dysprosium or terbium; and (4) phosphorescent crystals such as ruby, Cr-YAG, alexandrite, or phosphorescent mixed oxides such as magnesium fluoro-germanate. Examples of suitable indicator dyes which are sensitive to a gas and which show a short decay time include 8-Hydroxypyrene-1,3,6-trisulfonic acid, trisodium salt (HPTS), fluorescein, rhodamine B, rhodamine B-octadecyl ester, hexadecyl-acridine orange, hydroxymethyl coumarin, rhodamine, B-octadecyl ester, rhodamine B, naphthofluorescein, sulforhodamine 101, eosin, thionin, and Nile blue. In further specific embodiments, the present invention relates to combinations of reference dyes and indicators dyes, including all combinations of the above indicated exemplified indicators dyes and references dyes. Preferred examples of combinations of reference dyes and indicators dyes to be used in a chemo-optical sensor unit according to the invention include (reference dye/indicator dye): Ruthenium(II)-(tris-4,7-diphenyl-1,10-phenantroline)/HPTS; Ruthenium(II)-(tris-4,7-diphenyl-1,10-phenantroline)/fluorescein; Ruthenium(II)-(tris-4,7-diphenyl-1,10-phenantroline)/rhodamine B; Ruthenium(II)-(tris-4,7-diphenyl-1,10-phenantroline)/rhodamine B-octadecyl ester; Ruthenium(II)-(tris-4,7-diphenyl-1,10-phenantroline)/hexadecyl-acridine orange; Europium (III)-tris-theonyl-trifluoromethyl acetonate/hydroxymethyl coumarin; Platinum (II)-tetraphenylporphyrin/rhodamine B-octadecyl ester; Platinum (II)-tetraphenyl porphyrin/rhodamine B; Platinum (II)-tetraphenyl porphyrin/naphthofluorescein; Platinum (II)-tetraphenyl porphyrin/sulforhodamine 101; Platinum (II)-octaethyl porphyrin/eosin; Platinum (II)-octaethyl porphyrin/thionin; Platinum (II)-octaethyl ketoporphyrin/Nile blue; CR (III)-YAG/Nile blue; and Cr (III)-YAG/naphthofluorescein.

On the basis of a two dye combination in the sensor layer a measurement according to the Dual Lifetime Referencing principle, e.g. as derivable from U.S. Pat. No. 6,602,716 B1 or from Kocincova, New pH Sensitive Sensor Materials; Luminescent Fiber-Optic Dual Sensors for Non-Invasive and Simultaneous Measurement of pH and pO2 (Dissolved Oxygen) in Biological Systems, 2007, PhD thesis, University of Regensburg, may be implemented. In particular, on the basis of the different decay times of the indicator and the reference dye, the intensity of the excitation may be modulated at a fixed frequency and the phase angle of the luminescence signal, which is independent of the amplitudes, may be detected and translated into a relative intensity of the gas-sensitive dye (indicator dye) from which subsequently the gas concentration may be determined.

Accordingly, the sensing layer may be at least passable for gas molecules such as $O_2$ and/or $CO_2$, which may arrive from a deeper layer such as the gas-permeable layer. Typically, the sensing layer may also be permeable for water molecules, which may diffuse in or out of deeper layers, i.e. layers below the sensing layer according to the osmotic pressure in the corresponding region of the chemo-optical sensor according to the present invention.

The sensing layer may further be permeable for a first compound other than gas molecules and water according to the present invention, e.g. for molecules larger than a water molecule, e.g. having a size of about 1.5×, 2×, 3×, 4×, 5×, 10× or 15× or more of the size of a water molecule. It is preferred that the sensing layer allows the uptake of such compounds via diffusion from neighboring layers, e.g. the gas-permeable layer, or indirectly from a contact medium. It is preferred that the diffusion process is initiated by a contact medium, which comprises a first compound other than water according to the present invention, or by a conditioning fluid which comprises a first compound other than water according to the present invention. Such a diffusion into the sensing layer may be a slow diffusion due to the structure and/or chemical composition of the sensing layer, due to the size of the compound, or due to the polarity situation in the sensing layer. The diffusion rate and the amount of diffused material into and through the sensing layer may depend on the concentration of the first compound used, its chemical properties, e.g. its polarity, as well as its three-dimensional form.

In a further particularly preferred embodiment, the sensing layer may comprise a first compound other than water according to the present invention, e.g. a molecule larger than a water molecule, e.g. having a size of about 1.5×, 2×, 3×, 4×, 5×, 10× or 15× or more of the size of a water molecule. The sensing layer may, for example, comprise water and a first compound according to the present invention. The first compound other than water may have arrived at the sensing layer due to diffusion processes from the contact medium as defined herein. In a specific embodiment, the present invention relates to a chemo-optical sensor with a sensing layer comprising a first compound other than water in a concentration of about 1000 to 10,000 mOsm/kg, e.g. a concentration of about 1000, 1500, 2000, 2500, 3000, 3500, 4000, 4500, 5000, 5500, 6000, 6500, 7000, 7500, 8000, 8500, 9000, 9500 or 10,000 mOsm/kg.

In a further embodiment, the sensing layer may comprise a first compound other than water according to the present invention which has may be the result of a conditioning process, which includes at least the step of contacting said chemo-optical sensor comprising the sensing layer with a conditioning fluid comprising said first compound other than water according to the present invention. The contacting step may be carried out for sufficient time to allow for the diffusion of said first compound from the conditioning fluid to the sensing layer of the chemo-optical sensor unit. It is preferred that the first compound other than water is present, after the contacting step, in such a concentration in the sensing layer that the optical response of the chemo-optical sensor unit is stable when said chemo-optical sensor unit is employed on the skin, e.g. being in contact with a contact medium as defined herein, which in turn is in contact with the skin, wherein said contact medium has a constant gas concentration.

The arrival at the envisaged end point of the diffusion step may be tested by any suitable molecular, chemical, or physical test known to the skilled person. Preferably, the end point of the diffusion may be tested by analyzing whether the optical response of the chemo-optical sensor unit is stable when said chemo-optical sensor unit is employed on the skin, in particular, when the chemo-optical sensor is in contact with a contact medium as defined herein.

In certain specific embodiments, the sensing layer may comprise luminescent material which is capable of measuring the concentration of different gases, or which is capable of measuring the concentration of more than one gas simultaneously, e.g. the concentration of two gases at the same time. For example, the sensing layer may comprise two kinds of luminescent material adapted to the measurement of a different gas, respectively. Preferably, one sub-layer, region or one kind of material may be adapted to detect oxygen and a second sub-layer, region or kind of material is adapted to detect $CO_2$. Further details on multiparameter sensors and additional possibilities of implementing them would be known to the skilled person or can be derive from suitable literature sources such as WO 02/056023 or Schäferling, The Art of Fluorescence Imaging with Chemical Sensors, 2012, Angewandte Chemie International Edition, 51(15), 3532-3554.

The sensing layer may be provided as single layer. In alternative embodiments more than one sensing layer may be provided. Such second or further sensing layer may have the same properties or different properties than the first sensing layer. For example, the second or further sensing layer may comprise different luminescent material, e.g. different dyes, or it may be provided in a different chemical environment such as a different buffer, or having a different pH than a first sensing layer. In further embodiments, a second or subsequent sensing layer may be adapted to measure a different gas, than a first sensing layer, e.g. $O_2$ instead of $CO_2$ which may be measured in a first sensing layer.

The chemo-optical sensor unit may further be adapted to measure an optical response of the at least one sensing layer. Importantly, the received optical response is supposed to depend on the concentration of the gas to be measured. Such an adaption may comprise the provision of suitable detection methods or devices allowing to receive, detect and/or analyze one or more optical responses emanating from the sensing layer. The detection may be performed or implemented according to any suitable detection methods or on the basis of any suitable detection devices or comprising suitable components allowing to perform detection steps or sub-steps.

The term "gas-permeable layer" as used herein refers to a structure which is passable for gas molecules. Typically, the gas-permeable layer is provided as a membrane structure which is adapted to pass gas to the overlaying sensing layer. In specific embodiments, the gas-permeable layer is passable for gas molecules such as $O_2$ and/or $CO_2$. Typically, the gas-permeable layer may also be permeable for water molecules, which may diffuse in or out of layers above or below the gas-permeable layer, e.g. according to the osmotic pressure in the region of the chemo-optical sensor according to the present invention. Such diffusion process or transport of water molecules may, for example, be accomplished on the basis of water in the gas-phase.

The gas-permeable layer may further be permeable for a first compound other than water according to the present invention, e.g. for molecules larger than a water molecule, e.g. having a size of about 1.5×, 2×, 3×, 4×, 5×, 10× or 15× or more of the size of a water molecule. The permeability of the gas-permeable layer for a first compound other than water may preferably be a permeability for said first compound being dissolved in a liquid, e.g. for a first compound being dissolved state in an aqueous solution. It is preferred that the gas-permeable layer allows the uptake of such compounds via diffusion from neighboring layers, e.g. a contact medium which is present between the gas-permeable layer and the skin. It is preferred that the diffusion process is initiated by a contact medium, which comprises a first compound other than water according to the present invention, or by a conditioning fluid which comprises a first compound other than water according to the present invention. Such a diffusion into the gas-permeable layer may be a slow diffusion due to the structure and/or chemical composition of the gas-permeable layer, due to the size of the first compound other than water, or due to the polarity situation in the gas-permeable layer. The diffusion rate and the amount of diffused material into and through the gas-permeable layer may depend on the concentration of the first compound other than water used, its chemical properties, e.g. its polarity, the viscosity of the mixture, as well as its three-dimensional form.

In a further particularly preferred embodiment, the gas-permeable layer may comprise a first compound other than water according to the present invention, e.g. a molecule larger than a water molecule, e.g. having a size of about 1.5×, 2×, 3×, 4×, 5×, 10× or 15× or more of the size of a water molecule. The gas-permeable layer may, for example, comprise water and a first compound according to the present invention. The first compound may have arrived at the gas-permeable layer due to diffusion processes from the contact medium as defined herein. In a specific embodiment, the present invention relates to a chemo-optical sensor with a gas-permeable layer comprising a first compound other than water in a concentration of about 1000 to 10,000 mOsm/kg, e.g. a concentration of about 1000, 1500, 2000, 2500, 3000, 3500, 4000, 4500, 5000, 5500, 6000, 6500, 7000, 7500, 8000, 8500, 9000, 9500 or 10,000 mOsm/kg.

In a further embodiment, the gas-permeable layer may comprise a first compound other than water according to the present invention which has may be the result of a conditioning process, which includes at least the step of contacting said chemo-optical sensor comprising the gas-permeable layer with a conditioning fluid comprising said first compound other than water according to the present invention. The contacting step may be carried out for sufficient time to allow for the diffusion of said first compound other than water from the conditioning fluid to the gas-permeable layer of the chemo-optical sensor unit. It is preferred that the first compound other than water is present, after the contacting step, in such a concentration in the gas-permeable layer that the optical response of the chemo-optical sensor unit is stable when said chemo-optical sensor unit is employed on the skin, e.g. being in contact with a contact medium as defined herein, which in turn is in contact with the skin.

The arrival at the envisaged end point of the diffusion step may be tested by any suitable molecular, chemical, or physical test known to the skilled person. Preferably, the end point of the diffusion may be tested by analyzing whether the optical response of the chemo-optical sensor unit is stable when said chemo-optical sensor unit is employed on the skin, in particular, when the chemo-optical sensor is in contact with a contact medium as defined herein.

The membrane of the gas-permeable layer may be composed of suitable gas and water permeable material. For example, the membrane may be a silicone membrane, or may comprise silicone. Alternatively, the membrane may be composed of or comprise materials such as PTFE (teflon) or derivatives. In further alternative embodiments, the membrane may be composed of or comprise a metal mesh, porous hydrophobic polymers, e.g. based on polypropylene and ethylene, porous hydrophobic silicium oxides such as areogels, or perfluoro materials such as nafion. Further suitable material would be known to the skilled person and are also envisaged in the context of the present invention.

The gas-permeable layer may further be composed of filler material which is passable for gas molecules. An example of such filler material is silicone rubber material. In a preferred embodiment, the gas-permeable layer may thus comprise silicone rubber or essentially consist of silicon rubber material.

In further preferred embodiments of the present invention, the gas-permeable layer may additionally be adapted to prevent light from passing through the gas-permeable layer. The term "preventing light from passing through the gas-permeable layer" is in particular intended to mean that the gas permeable layer is be adapted to reflect or scatter light transmitted through the at least one sensing layer, and/or to block possible light interferences outside of the intended sensor range. The reflection or scattering of light by the gas permeable layer may be achieved by using any suitable light reflecting material such as metals, e.g. aluminium, or metal oxides. Particularly preferred is the use of titanium compositions, e.g. compositions comprising $TiO_2$. In specific embodiments, the light reflection or scattering may be complete, i.e. for all wavelengths, or it may be specific for certain wavelengths or ranges of wavelengths. For example, light of a certain wavelength or range of wavelengths, in particular of the excitation wavelength for the luminescent material in the sensing layer, may be reflected or scattered, whereas light of a different wavelength which is not excitatory for the luminescent material in the sensing layer may not be reflected. In further embodiments, the light reflection or scattering may be dependent on specific parameters, e.g. temperature, pH, presence of gas molecules, presence of polar compounds etc. at the gas-permeable layer. Further, the gas permeable layer may block possible interference of fluorescent molecules, for example outside of the intended sensor range. In a preferred embodiment, the blocking of interference of fluorescent molecules may be a blocking of fluorescence outside of a range of about 400 nm-700 nm. Such a blocking activity may be accomplished by providing light absorbing materials, which work outside of the envisaged sensing range.

The gas-permeable layer may thus essentially function as barrier to light, as permeable layer for small molecules such as $CO_2$, $O_2$ or $H_2O$, and as semi-active, i.e. strongly retarding, barrier to larger molecules, in particular a first compound other than water according to the present invention, which may have a low polarity.

The gas-permeable layer may be provided as single layer. In alternative embodiments more than one gas-permeable layer may be provided. Such second or further gas-permeable layer may have the same properties as, or different properties than the first gas-permeable layer. For example, the second or further gas-permeable layer may have the property of reflecting light of a different wavelength. In further embodiments, the second or further gas-permeable layer may have the property of being permeable for different molecules than the first gas-permeable layer. E.g. different gases, or different compounds may pass through the first and second or subsequent gas-permeable layer.

In further specific embodiments of the invention the chemo-optical sensor may further comprise at least one optical transparent layer adjacent to the at least one sensing layer. The optical transparent layer may preferably be on top of the sensing layer, which in turn is on top of the gas-permeable layer as defined herein above. The transparent layer may accordingly cover the sensing layer and protect it from direct contact with the surrounding atmosphere. Thus, the at least one sensing layer may be enclosed by the gas permeable layer from one side and by the optical transparent layer from the other side. The term "optical transparent layer" as used herein refers to a carrier substrate which is at least partially transparent for radiation. In some embodiments, the optically transparent layer may be transparent for the entire suitable spectrum of electromagnetic waves, e.g. infrared light, visible light and ultraviolet light. In other embodiments, the optically transparent layer may be transparent for specific wavelengths or wavelength ranges only. The optical transparent layer may for example be transparent for the predetermined radiation as described above, or excitation wavelength(s) or wavelengths range(s) for the luminescent material(s) in the sensing layer, whereas light of a different wavelength which is not excitatory for the luminescent material in the sensing layer may not be passed. In addition, the optical transparent layer may be transparent for the light of the optical response generated in the sensing layer. Such light may be provided in a specific wavelength or range of wavelength which may specifically be passed through the optical transparent layer, whereas light of different wavelengths may be passed. In a specific embodiment, the optical transparent layer may only be transparent for excitation wavelength(s) or ranges of wavelength(s) for the luminescent material in the sensing layer and for the wavelength(s) or range of wavelength(s) generated as optical response by said luminescent material in the sensing layer The optical transparent layer may be composed of any suitable transparent material known to the skilled person. The optical transparent layer may, for example, be composed of transparent material such as glas, polycarbonate, PET, silicone rubber, or PMMA (plexiglas).

In further embodiments, the optical transparent layer may be non-permeable for gas, e.g. for $O_2$ and/or $CO_2$. In further embodiments, the optical transparent layer may further low-permeable for water and/or a first compound other than water according to the present invention.

In a central aspect the present invention provides a chemo-optical sensor unit as defined herein which is adapted to operate with a contact medium between the gas-permeable layer and the skin. The term "contact medium" as used herein refers to a medium which may be provided at the interface between the chemo-optical sensor unit and the surface layer on which the measurement of gas is to be carried out, i.e. the skin. Preferably, the contact medium is interposed at least between the gas-permeable layer as defined herein above and the surface layer on which the measurement of gas is to be carried out, i.e. the skin of the human or animal body. The contact medium may be a gel or liquid, which typically allows the transfer gas molecules from the deeper layer, e.g. skin, to the chemo-optical sensor unit according to the present invention. Thus, in a particularly preferred embodiment, the contact medium is at least gas-permeable. The gas-permeability may be a general permeability for any gaseous material. Alternatively, the contact medium may have a specific permeability for certain gas molecules, e.g. for $O_2$, $CO_2$, $CO$, $N_2$, or $NH_3$. Particularly preferred is the permeability for $O_2$ and/or $CO_2$. Most preferred is the permeability for $CO_2$. In specific embodiments, the contact medium may be selectively permeable for certain gases and impermeable for other gases. It is preferred that the contact medium by selectively permeable for at least $O_2$ and/or $CO_2$. Most preferred is a selective permeability for $CO_2$.

Furthermore, the contact medium may allow to keep the water content or moisture content of the surface layer on which the measurement of gas is to be carried out stable, or to control the water content or moisture content of the surface layer on which the measurement of gas is to be carried out, e.g. the skin of the human or animal body. Advantageously, the contact medium may comprise a first compound other than water according to the present invention, for which a sensing layer and/or a gas-permeable layer as defined herein may be permeable. The contact medium may accordingly provide said first compound other than water in a concentration high enough to allow a diffusion of said first compound out of the contact medium into adjacent layers such as the at least one gas-permeable layer of the chemo-optical sensor unit, or the at least one sensing layer of the chemo-optical sensor unit.

The contact medium is, in further embodiments, characterized as being biocompatible. The term "biocompatible" as used herein means that the contact medium does not cause a toxic, immunologic, and/or allergic reaction to the surface area of the skin of the human or animal body to which it is applied, or to the body of the person to which it is applied, or any other biologically or medicinal deleterious or harmful reaction, e.g. that it is not carcinogenic.

The contact medium may, in further embodiments, alternatively or additionally be capable of penetrating the chemo-optical sensor unit. The "penetration" may preferably be the provision of moveable elements provided in the contact medium, in particular of the first compound other than water according to the present invention. Said first compound may, for example, be present in the contact medium in an amount or in a concentration together with suitable carrier forms which allows a diffusion out of the contact medium and into the adjacent layers of the chemo-optical sensor unit, e.g. the gas-permeable layer or the sensing layer.

In addition, the contact medium may be thermally conductive. The thermal conductivity may be used to mitigate thermal changes of the chemo-optical sensor unit, i.e. to minimize a temperature difference between the chemo-optical sensor and the skin area underlying the contact medium. Thereby a constant temperature at the chemo-optical sensor unit can be achieved, thus allowing for an accurate measurement of the concentration of a gas.

In an embodiment the present invention provides a chemo-optical sensor unit as defined herein which is provided in a conditioning fluid. The provision may be, for example, a packaging, storing, keeping, suspending of the chemo-optical sensor in the conditioning fluid. This may be a short term activity, e.g. of 10 to 60 minutes, or 1 to 24 h, or a longer term activity of 1 day to several months or years, e.g. 2 months, 3 months, 4 months, 5 months, 6 months, 12 months, 24 months or more or any time period in between the indicated values.

The term "conditioning fluid" as used herein refers to a liquid or gel-like substance, which keeps the chemo-optical sensor unit in state which allows its immediate use or application without previous calibration steps. The conditioning fluid may, for example, allow to keep the water content or moisture content of the surface layer on which the measurement of gas is to be carried out stable. In a preferred embodiment, the conditioning fluid may comprise a first compound other than water according to the present invention, for which a sensing layer and/or a gas-permeable layer as defined herein may be permeable. The conditioning fluid may accordingly provide said first compound other than water in a concentration high enough to allow a diffusion of said first compound out of the conditioning fluid into adjacent layers such as the at least one gas-permeable layer of the chemo-optical sensor unit, or the at least one sensing layer of the chemo-optical sensor unit. The conditioning fluid may further be biocompatible, i.e. it may be non-toxic, non-immunogenic, and/or non-allergenic. In specific embodiments, toxic, immunologic or allergic reactions caused by ingredients of the conditioning fluid may be mitigated or blocked by the presence of counter activities, e.g. the blocking agents, antidotes etc.

The conditioning fluid may, in further embodiments, alternatively or additionally be capable of penetrating the chemo-optical sensor unit. The "penetration" may preferably be the provision of moveable elements provided in the conditioning fluid, in particular of the first compound other than water according to the present invention. Said first compound may, for example, be present in the conditioning fluid in an amount or in a concentration together with suitable carrier forms which allows a diffusion out of the conditioning fluid and into the adjacent layers of the chemo-optical sensor unit, e.g. the gas-permeable layer or the sensing layer.

In a specific embodiment of the present invention, the conditioning fluid is similar to the contact medium, e.g. comprising most of the components of the contact medium. In further preferred embodiments, the conditioning fluid is essentially identical to the contact medium as defined herein, or is identical to the contact medium as defined herein. Accordingly, a chemo-optical sensor as defined herein may be stored, kept, packaged etc. in contact medium as defined herein.

In a particularly preferred embodiment, the contact medium and/or the conditioning fluid comprises at least a first compound other than water. A "first compound" as used herein means a compound, which is principally capable of diffusing or moving out of the contact medium and penetrating adjacent layers, e.g. of the chemo-optical sensor unit according to the present invention. Such a compound does not include water. It is preferred that the first compound is hygroscopic, i.e. that it is capable of bringing and/or keeping water in its environment, e.g. the contact medium and/or the adjacent layer(s) of the chemo-optical sensor. It is further preferred that the first compound has a high osmotic buffer capacity. Thereby, an influence on the skin and/or on the sensor may be reduced or minimized. In specific embodiments, the first compound being present in the contact medium or the conditioning fluid may also be capable of penetrating body surface layers, i.e. the skin. Preferred examples of such compounds include organic molecules. It is also envisaged that such compounds are polar molecules in general, in particular polar molecules of a small size, e.g. 1.5×, 2×, 3×, 4×, 5×, 10× or 15× the size of a water molecule. Examples include, for instance, cations, anions. In preferred embodiments, the first compound other than water is a polyhydroxy alkane or an alcohol, e.g. an alcohol derived from short-chained alkanes or alkenes. It is preferred that the first compound other than water is a $C_2$-$C_{10}$ alcohol, e.g. a $C_2$ alcohol, a $C_3$ alcohol, a $C_4$ alcohol, a $C_5$ alcohol, a $C_6$ alcohol, a $C_7$ alcohol, a $C_8$ alcohol, a $C_9$ alcohol or a $C_{10}$ alcohol. Also envisaged, in alternative embodiments, is the employment of larger alcohol molecules, e.g. $C_{11}$ to $C_{15}$ alcohols, or alcohols with more than 15 C-atoms. Further envisaged is the use of derivatives of these alcohols.

Additional examples of compounds being present in the contact medium or the conditioning fluid include a polysaccharide. In further specific embodiments, the first compound may be a protein, e.g. albumin. In yet another preferred embodiment of the present invention the first compound is a carbohydrate, e.g. glucose or sucrose, a reduced carbohydrate or a derivative thereof.

It is particularly preferred that the first compound other than water being present in the contact medium or the conditioning fluid is sorbitol, a sorbitol derivative, glycerol, a glycerol derivative, xylitol, or a xylitol derivative, glycol or a glycol derivative. The most preferred first compound other than water is propylene glycol. In specific embodiments, the first compound other than water may also be ethylene glycol, which is known to be toxic for human beings. Ethylene glycol may accordingly be used for applications in environments in which it is not in contact with the body, or its concentration in the contact medium or conditioning fluid may be reduced such that the toxic effect is mitigated or reduced.

The contact medium as defined herein thus advantageously provides the functionality of a balancing means between the chemo-optical sensor unit and the underlying surface, e.g. skin surface, facilitating gas exchange and avoiding chemical or osmotic molecular perturbations in the chemo-optical sensor unit. By providing a first compound other than water in the contact medium, which penetrates the chemo-optical sensor unit, or which is present in the chemo-optical sensor unit and/or in the skin sector to be analysed, e.g. in essentially the same concentration as in the contact medium, the osmotic environment inside and outside of the chemo-optical sensor unit (at least with respect to the surface to be analysed, i.e. below the chemo-optical sensor unit) becomes balanced. It is accordingly possible detecting the concentration of gas in the skin without compromising the sensitivity of the method due to water transport in the sensor unit. This advantageously helps avoiding calibration or recalibration steps during the use of the chemo-optical sensor unit. The above mentioned first compound other than water may be provided in any suitable concentration in the contact medium or the conditioning fluid. For example, propylene glycol may be provided in an amount of 10%, 15%, 20%, 25%, 30%, 35%, 36%, 37%, 38%, 39%, 40%, 45%, 50%, 55%, 60%, 65%, 70%, 75%, 80%, 85% by volume of the contact medium or conditioning fluid.

In a further preferred embodiment, the first compound other than water according to the present invention may be present in the chemo-optical sensor, e.g. in the sensing layer and/or the gas-permeable layer, in such a concentration that the optical response of the chemo-optical sensor unit is stable when said chemo-optical sensor unit is employed on the skin, e.g. being in contact with a contact medium as defined herein, which in turn is in contact with the skin. The first compound other than water as defined herein thus advantageously provides the functionality of a balancing means between the chemo-optical sensor unit, the contact medium and the underlying surface, e.g. skin surface, facilitating gas exchange and avoiding chemical or osmotic perturbations due molecular perturbations such as movement of water out of the chemo-optical sensor unit and/or in or out of the surface layer to be analysed, i.e. skin surface. It is accordingly possible detecting the concentration of gas in the skin without compromising the sensitivity of the method due to molecular perturbations in the chemo-optical sensor unit. As a result the detectable optical response is received in a stable manner, which does not alter due to molecular perturbations such as water transport etc. The stability of the response may, for example, be tested with a device as described herein. In further embodiments, the stability may be tested by sampling from a batch and by an in vitro testing. Such a test may, for example, comprise the exposure of the sensor to a fixed $CO_2$ concentration induced in a contact medium, e.g. as described herein.

Further envisaged is the possibility to use any combination of the above mentioned compounds or compound categories. Accordingly, a first compound other than water as outlined above may be combined with a second or third compound differing from the first compound, being selected from the compounds or compound categories mentioned above.

In further preferred embodiments, the contact medium or conditioning fluid may comprise a first compound other than water and an additional element or second compound. The additional element or second compound may be water and therein dissolved NaCl, i.e. Na$^+$ and Cl$^-$ ions of a NaCl solution. It is preferred that the NaCl solution is a physiological saline. The concentration of the NaCl solution may be of any suitable value. For example, a concentration of about 9 g/liter NaCl may be used.

It is particularly preferred using a combination of propylene glycol with a NaCl solution. The combination may comprise any suitable proportions of propylene glycol and NaCl in water. For example, about 10% to 90% propylene glycol and NaCl in water may be used. The amount for propylene glycol in the NaCl water solution may be, for example, 10%, 15%, 20%, 25%, 30%, 35%, 36%, 37%, 38%, 39%, 40%, 45%, 50%, 55%, 60%, 65%, 70%, 75%, 80%, 85% by volume, or more or any value in between the indicated values. Particularly preferred is the combination of 37% propylene glycol and 9 g/liter NaCl in water.

In a further embodiment the chemo-optical sensor of the present invention comprises or includes a contact medium or a conditioning fluid as defined herein above, or consists of a combination of the elements of the chemo-optical sensor mentioned herein above, e.g. at least one sensing layer and at least one gas-permeable layer, and a contact medium as defined herein above.

The chemo-optical sensor according to the present invention is suitable for transcutaneous measurement. The chemo-optical sensor unit may, in specific embodiments, also be used for different measurement purposes, e.g. in the context of microbiological or biotechnological production processes. Preferably, the chemo-optical sensor unit is a transcutaneous sensor unit. The term "transcutaneous sensor unit" as used herein means that the sensor is to be applied or can be applied on the skin. Accordingly, the sensor is capable of measuring blood gas concentrations of a subject via the subject's skin, wherein blood gas may diffuse via the skin into the chemo-optical sensor unit passing a contact medium as defined herein above. The term "blood gas" as used herein refers to gaseous materials present in the blood and capable of exiting a body, which can be measured, e.g. over the skin. The measurement is such that a chemically exact reflection of the gas content of blood is obtainable. The preferred blood gas concentrations to be measured are the concentrations of $O_2$ or $CO_2$. Particularly preferred is the measurement of the concentration of $CO_2$.

In another embodiment of the present invention, the chemo-optical sensor unit as defined herein above may comprise additional components or be combined with additional components.

For example, the chemo-optical sensor may be combined with or comprise at least one light source which is adapted to irradiate the sensing layer as defined herein above. The light source may provide radiation in a predetermined wavelength, preferably light in an excitation wavelength or range of wavelengths adapted to the dye or dyes present in the sensing layer. The light source may have any suitable form, provide any suitable intensity and provide any suitable wavelength(s). The light source may preferably be a light emitting diode (LED).

In a further optional embodiment, the light source may additionally be combined with a light guiding structure. The light guiding structure may be arranged, for example, above the sensing layer/optically transparent layer of the chemo-optical sensor and may be connected to a light source external to the chemo-optical sensor unit, e.g. as defined above. Light from an external light source may be introduced into the light guiding structure, which is adapted to direct said light towards the at least one sensing layer. The light-guiding structure may comprise any suitable light guiding material. Preferably, optical fibers may be used as light guiding material, which may be provided in the form of light-guiding structures. Optical fibers may accordingly be provided as single fibers, or as fiber bundles. A light source, being connected to a light guiding structure, may thus be used to irradiate the sensing layer of a chemo-optical sensor unit according to the present invention, although being located externally. In further embodiments, a light source may be connected to more than one chemo-optical sensor unit via light guiding structures arriving at distinct sensor units.

The chemo-optical sensor may further be combined with a detection device. Such a detection device, for instance a photosensitive device, may be capable of sensing an optical response coming from the sensing layer and may be adapted to generate signals, e.g. electrical signals, corresponding to the sensed optical response. The signals may further be transmitted to an external apparatus for subsequent analysis. The detection device may be adapted to the optical response expected from the sensing layer, e.g. provided by a dye or a combination of dyes as described herein above.

The detection device may further be combined via a light guiding structure to the chemo-optical sensor unit as defined herein. In specific embodiments the same light guiding structure, which provides light from the light source to the sensing layer, may be used to collect the optical response of the sensing layer and to guide said optical response, for instance fluorescent light, via the same or a different optical fiber to a detection device or an apparatus external to the chemo-optical sensor unit for analysis. By using light guiding structures it is thus possible to connect an input and/or output light guiding structure, which is/are coupled to the chemo-optical sensor unit. In this embodiment no additional unit needs to be connected to the chemo-optical sensor unit accommodating the light source and the at least one detection device.

In specific embodiments, the light may thus be transferred into the sensing layer and luminescence, e.g. fluorescence light, may be collected through the same surface of the sensing layer. Alternatively, a light guiding structure connected, for example, via optical fibers to a light source which may be external to the chemo-optical sensor unit, may be used to direct light from an external light source and transmitted through at least one optical fiber towards the at least one sensing layer. At least one detection device, for instance a photosensitive device, may then be included to sense an optical response and may be adapted to generate e.g. electrical signals corresponding to the sensed optical response. Said signals may be transmitted to an external device for analysis. Alternatively, the chemo-optical sensor unit may be adapted to perform said analysis and to output the analysis results to some external device.

Preferably, the at least one light source and the at least one detection device may form a unit. This unit may in a further preferred embodiment be detachably connected to the chemo-optical sensor unit, e.g. by a housing or structure. Accordingly, certain parts of the chemo-optical sensor unit, for instance the sensing layer, gas permeable layer, or a housing and/or supporting structure of the chemo-optical sensor unit may be disposable, whereas other parts of the optical sensor such as the light source and the detection device, or the light guiding structures and may be reused. This reduces costs, since expensive parts such as light sources and/or detection devices and/or electronics do not have to be replaced and can be reused.

In specific embodiment, the chemo-optical sensor unit may be composed of two devices or two parts, a disposable or cartridge part and a non-disposable or reusable part. In particular, the disposable or cartridge part may work as passive device and not include any expensive electronics at all. Hence, this part may be manufactured with low effort thereby reducing costs, whereas the second, non-disposable part may include the electronics or optical elements and be reused. It may accordingly also be uses with different disposable parts, e.g. allowing to measure the concentration of different gases (for instance $O_2$ and $CO_2$). Thereby an increased flexibility of the chemo-optical sensor unit can be provided.

Another example of an additional component, which may be combined with the chemo-optical sensor as described above is at least one heating element. Additionally, or alternatively, the chemo-optical sensor may comprise at least one temperature sensor. If, for example, the chemo-optical sensor unit is attached to a person's skin, the heating element may be adapted to increase blood perfusion and gas permeability of the skin, thereby increasing sensitivity and accuracy of the chemo-optical sensor unit, in particular its transcutaneous application. The heating element may be in any suitable form, e.g. could be in the form of a diode or may comprise a thin foil to minimize optical distances and thermal mass. Alternatively, the heating element may be a resistance heater or diode so that the heating element can also be used as a temperature sensor, i.e. heating element and temperature sensor are formed by the same device. This advantageously may reduce costs and space required for installation of a heater and temperature sensor. In further embodiments, the temperature sensor may be realized as a separate element for sensing the temperature of the chemo-optical sensor unit, e.g. in order to avoid injuries or burnings of the skin. During operation the temperature of the heating element and of the contact medium and sensing layer may be increased by the heating element to a temperature in the range of 42° to 45° C. This temperature range may increase capillary blood flow in the skin and bring the capillary blood gas levels close to the arterial blood gas levels. During operation the sensor temperature may accordingly be measured by at least one temperature sensor as defined above, included in the heating element and/or the contact element and/or by a separately provided temperature sensor. The temperature may be controlled such as to have a well defined measurement condition and to prevent burning of the skin.

In further specific embodiments, temperature sensors and/or heating elements may be provided as non-disposable or reusable parts of the chemo-optical sensor unit. The temperature sensors and/or heating elements may accordingly be detachably connected to other elements of the chemo-optical sensor unit as defined herein above.

In another aspect the present invention relates to a system relates to a system for patient monitoring and/or ventilation of a patient, comprising a chemo-optical sensor unit as defined herein above, a ventilation device and/or a monitoring device.

The monitoring device may, for example, include optoelectronics for supplying the chemo-optical sensor unit with light via optical fibers, and for receiving luminescent light from the sensing layer. The monitoring device may further comprise means for determining/calculating a gas concentration based on the received optical response, for instance light intensity of the luminescent light generated in the sensing layer. The monitoring device may further comprise a heater controller for controlling the temperature of the heating element. The heater controller may be adapted for detecting the temperature of the heating element using the temperature sensor included in the chemo-optical sensor unit and for adjusting for instance a current flowing through a resistance heater included in the heating element or the contact element based on the detected temperature. The monitoring device may additionally comprise means for communication with the ventilation device. Said communication means may include at least one communication technique, e.g. wired (cable), wireless (Bluetooth, infrared, RF), etc. In a preferred embodiment, the monitoring device comprises means for calculating/determining the gas concentration, in particular $O_2$ and most preferably $CO_2$, from the measured/sensed optical response of the sensing layer, for instance from the sensed intensity or decay time of the luminescent light. The analyzing device, e.g. monitoring device, may be based on the operation of an algorithm that may also be adapted to compensate, inter alia, for temperature effects for calculating/determining the gas concentration may use.

The ventilation device may include all functions associated of a typical ventilation device for invasive or non-invasive ventilation of a patient with respiratory failure. The ventilation device may, for example, comprise display means and a storage device for displaying and storing information/data received from the monitoring device. In particular, the display means of the ventilation device may be adapted to display a gas concentration, e.g. $O_2$ or $CO_2$, determined by the monitoring device and may further store gas concentration information over a predetermined time period for instance for later evaluation by a physician or for close loop adaptation of the ventilation settings. In another embodiment, the ventilation device may be controlled on the basis of the measured/determined concentration of gas.

In specific embodiments the chemo-optical sensor unit may be operationally coupled to a monitoring device and/or a ventilation device as defined herein above, wherein the monitoring device may be adapted to at least one of analyzing the optical response of the sensing layer, controlling the heating element and/or the temperature sensor, or displaying the determined gas concentrations, etc. The monitoring device or ventilation device may additionally include means for storing monitored data, e.g. as a function of time. These data can be made available at a later time for analysis by a physician, e.g. by transfer to a hospital computer system, or a physician's handheld diagnosis apparatus.

In yet another aspect the present invention relates to a method for conditioning a chemo-optical sensor unit for transcutaneous measurement of a concentration of a gas, comprising at least one sensing layer adapted to be irradiated with a predetermined radiation; and at least one gas-permeable layer adjacent to one side of the at least one sensing layer, adapted to pass gas whose concentration is to be measured through the gas-permeable layer towards the sensing layer; wherein said chemo-optical sensor unit is adapted to operate with a contact medium between the gas-permeable layer and the skin, wherein said contact medium comprises a first compound other than water; wherein said chemo-optical sensor unit is characterized in that said at least one gas-permeable layer and said at least one sensing layer are permeable to said first compound; and wherein the chemo-optical sensor unit is adapted to measure an optical response of the at least one sensing layer, whose optical response depends on the concentration of the gas; the method comprising contacting said chemo-optical sensor unit with a conditioning fluid. The conditioning fluid to be used is the condition fluid as defined herein above, i.e. a conditioning fluid which comprises a first compound other than water according to the invention. In specific embodiments, the conditioning is carried out with the contact medium as defined herein above.

The term "contacting" as used in the context of the method described above refers to process of entering a chemo-optical sensor, preferably the gas-permeable layer of a chemo-optical sensor as defined herein, into a conditioning fluid as defined above, e.g. a bath, bag or tube containing said conditioning fluid. The contacting may alternatively also be an application of said conditioning fluid directly onto the chemo-optical unit, e.g. by pipetting it on the relevant layer, e.g. the gas-permeable layer. Any additional, suitable ways or techniques of bringing the chemo-optical sensor unit and the conditioning fluid in contact, as known to the skilled person, are also envisaged by the present invention.

The contacting step may be carried out for sufficient time to allow the first compound other than water as defined herein above, e.g. propylene glycol, or a combination of propylene glycol and a physiological saline to diffuse into at least the gas-permeable layer of the chemo-optical sensor unit, i.e. to penetrate the chemo-optical sensor unit.

More preferably, the contacting is carried out until the first compound other than water as defined herein above, e.g. propylene glycol and/or physiological saline components have reached an equilibrium. The term "equilibrium" as used herein means that the first compound other than water as defined herein is present in the chemo-optical sensor unit, in particular in the adjacent layer of the chemo-optical sensor unit such as the gas-permeable layer and the sensing layer, and in the contact medium in essentially the same concentration such that essentially no further movement of the first compound, or of additional molecules such as water molecules, takes place.

In a further specific embodiment of the invention, an equilibrium may be considered to be given, if the first compound other than water is present in such a concentration in the sensing layer of the chemo-optical sensor unit that the relation between $CO_2$ concentration and optical response of the chemo-optical sensor unit is stable when said chemo-optical sensor unit is employed on the skin or in-vitro, in particular when being employed using a contact medium as defined herein, wherein said contact medium has a constant gas concentration. Accordingly, the equilibrium may further be understood as being given when the sensor response stabilizes when exposed to a constant $CO_2$ concentration.

In such a scenario the conditioning fluid is preferably identical to the contact medium or comprises the first compound other than water as defined herein above in the same amount or concentration, optionally also accompanied by the same buffer conditions, pH, or local structural elements as in the contact medium to be used.

The contacting step may be carried out, for example, for any suitable time period necessary. On the basis of practical experiments, a condition or contacting time of several days to several weeks is envisaged. For example, the contacting may be carried out for a time period of 1 week, 2 weeks, 3 weeks, 4 weeks, 5 weeks or a longer period or any time interval in between the indicated values. Preferred is a contacting time of about 4 weeks.

In a further aspect the present invention relates to a chemo-optical sensor unit obtainable by a method for conditioning the chemo-optical sensor unit as defined herein above. The accordingly obtained chemo-optical sensor unit may be regarded as being conditioned and thus directly usable for the transcutaneous measurements without previous calibration. Such a chemo-optical sensor unit may further be combined with further components such a light source or a detection device as described herein above, or it may be provided in the form of a system for patient monitoring as defined herein above. In further specific embodiments, the chemo-optical sensor may be provided as such or be provided with or comprise a contact medium as defined herein above, or the chemo-optical sensor may be provided with a conditioning fluid as defined herein above.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1—Effect of Propylene Glycol Studied in an In-Vitro Situation

Figure 2:
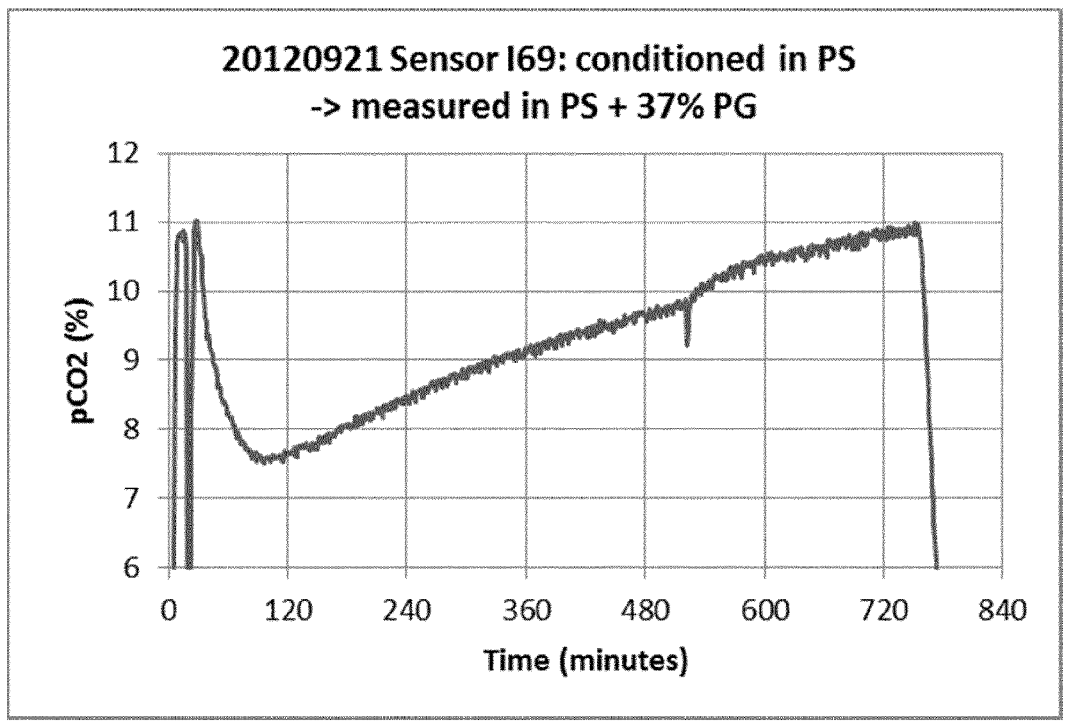
FIG. 2 shows data of an in vitro measurement at 10% $pCO_2$ in physiological saline (PS) and 37% propylene glycol of a sensor spot which was first conditioned in physiological saline (PS).

In a first experiment the effect of propylene glycol (PG) was studied in an in-vitro situation. Prior to the measurement, a PreSens $CO_2$ sensor spot was first pre-conditioned in a Physiological Saline (PS) (9 g/l NaCl) solution. After transfer to a test-solution comprising PS and 37% PG, 10% $CO_2$ and 90% $N_2$ is constantly bubbled through. FIG. 2 shows the observed response.

At the beginning of the experiment the sensor started at 11% $pCO_2$ and dropped in the first hour towards 7.5%. This effect can be explained by a sensitivity reduction of the spot related to water leaving the sensor due to the 20-fold higher osmotic pressure—due to the PG—of the test fluid. After 100 minutes said effect reversed and the sensor slowly rose towards the initial 11% level, indicating that the osmotic pressure between spot and test-fluid became balanced and that the water content inside the sensor normalised. As the PG concentration in the test-fluid was constant (due to its large volume compared to the sensor spot volume) it is deduced that PG transferred from the test fluid into the sensor.

The stable end-situation of the experiment after a few days showed a slightly increased sensitivity, probably caused by a small water excess compared to the nominal (isotone) situation or a direct effect of PG on the indicator dye in the sensor spot (not shown by FIG. 1).

The experimental data indicate that the PreSens $CO_2$ sensor can be conditioned in a solution comprising propylene glycol (PG).

Example 2—Effect of Propylene Glycol Studied in a Transcutaneous Situation

Figure 3:
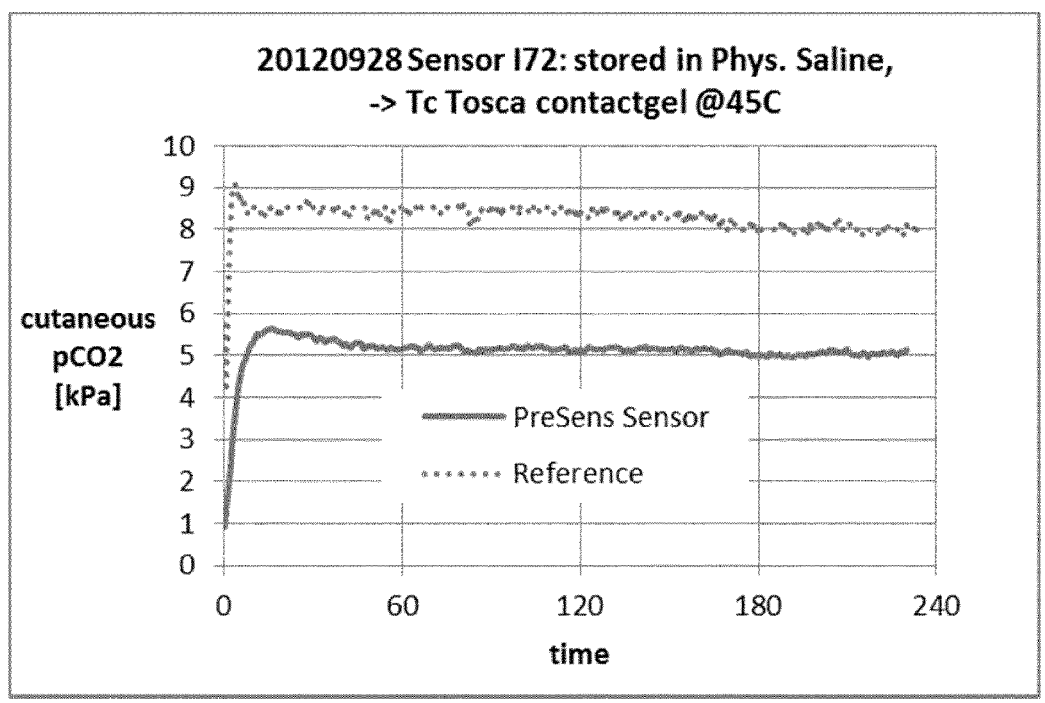
FIG. 3 shows data of a transcutaneous measurement in Radiometer TOSCA contact gel after pre-conditioning in a physiological saline. The figure provides measurement data for the PreSens sensor and the Radiometer TOSCA reference instrument.

In a second experiment the effect of propylene glycol (PG) in a transcutaneous measurement was studied. A dedicated sensor probe comprising a PreSens spot and a commercial Radiometer TOSCA transcutaneous $PtcCO_2/SpO_2$ probe for referencing were both placed on the under-arm of a test-person. Both sensors were heated up to 45° C. and comprised Radiometer TOSCA contact gel (~40% PG) between the sensor and the skin. Prior to the measurement, the PreSens spot was pre-conditioned in a Physiological Saline solution (9 g/l NaCl). FIG. 3 shows the obtained results.

The reduced sensitivity of the PreSens sensor can be explained by the fact that after application to the skin, (typically during the first 40 minutes) the much higher osmotic pressure of the contact gel extracts water from the spot.

At the same time, a small part of the propylene glycol will penetrate the skin while the moisturizing behavior of propylene glycol will prevent water from escaping the skin. The water extraction from the sensor spot and the skin penetration of propylene glycol lower the propylene glycol concentration in the contact gel—and thus its osmotic pressure—towards a more isotonic value, which is better in equilibrium with the sensor spot so that water transport stops. That is why the response stabilizes to a much lower, but fairly constant, cutaneous $pCO_2$ level compared to the reference sensor.

The actual sensitivity reduction is not well defined because it will depend on for instance the volume of propylene glycol in between sensor spot and skin.

Figure 4:
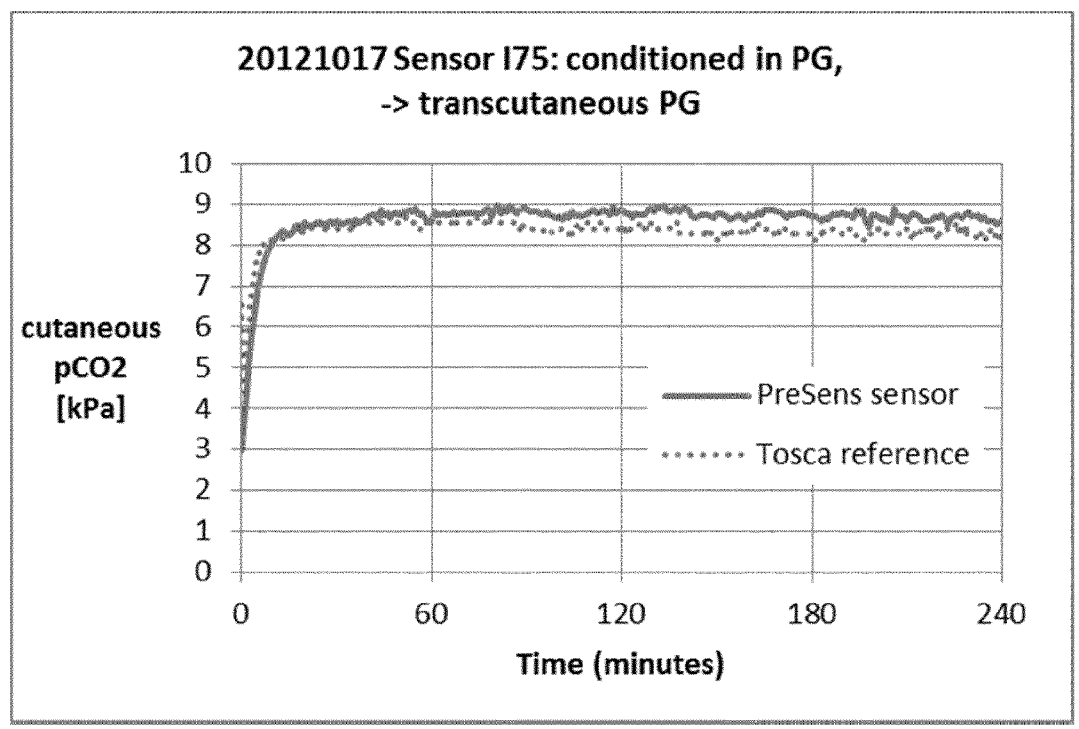
FIG. 4 shows data of a transcutaneous measurement after 6 days pre-conditioning in 37% Propylene Glycol and physiological saline after re-calibration. The figure provides measurement data for the PreSens sensor and the TOSCA reference.

Example 3—Effect of Propylene Glycol Studied in a Transcutaneous Situation after Pre-Conditioning FIG. 4 shows a transcutaneous measurement after 6 days conditioning of the spot in 37% propylene glycol and 9 g/l NaCl and re-calibration. The conditioning fluid was also used as contact medium between spot and skin. This measurement shows a stable result in good agreement with the Radiometer TOSCA reference sensor.

In this experiment both the Radiometer TOSCA reference sensor and the chemo-optical sensor were positioned on the same subject, close to each other. The signals measured with both, the Radiometer TOSCA reference sensor and the chemo-optical sensor, were stable and essentially provided the same information. However, the absolute levels detected with the Radiometer TOSCA reference sensor and the chemo-optical sensor were different. This difference is attributed to the fact that the calibration of the chemo-optical sensor has to be adapted to the conditioned situation since the presence of propylene glycol in the chemo-optical sensor changes the sensor calibration.

The invention claimed is:

1. A chemo-optical sensor unit for transcutaneous measurement of a concentration of a gas, comprising:
   at least one sensing layer adapted to be irradiated with a predetermined radiation;
   at least one gas-permeable layer adjacent to one side of the at least one sensing layer and adapted to pass gas whose concentration is to be measured through the at least one gas-permeable layer towards the at least one sensing layer;
   a contact medium configured to contact skin and, when the contact medium is in contact with the skin, is positioned between the at least one gas-permeable layer and the skin, wherein the contact medium comprises a first compound other than water, wherein the first compound is an organic compound, and wherein the chemo-optical sensor unit is characterized in that the at least one gas-permeable layer and the at least one sensing layer are permeable to the first compound; and
   at least one photosensitive detector adapted to measure an optical response of the at least one sensing layer to the predetermined radiation, wherein the optical response depends on the concentration of the gas.

2. The chemo-optical sensor unit of claim 1, wherein the at least one gas-permeable layer and/or the at least one sensing layer comprises the first compound.

3. The chemo-optical sensor unit of claim 1, wherein the contact medium is at least one of: gas-permeable, biocompatible, thermally conductive, and capable of at least partially penetrating the chemo-optical sensor unit.

4. The chemo-optical sensor unit of claim 1, wherein the first compound is a carbohydrate, a reduced carbohydrate, a polysaccharide, a polyhydroxy alkane or any derivative thereof, or a $C_2$-$C_{10}$ alcohol or a derivative thereof.

5. The chemo-optical sensor unit of claim 4, wherein the first compound is propylene glycol, xylitol, sorbitol or glycerol, or a derivative thereof.

6. The chemo-optical sensor unit claim 1, wherein the contact medium additionally comprises (i) water and (ii) dissolved sodium chloride.

7. The chemo-optical sensor unit of claim 1, wherein the at least one gas-permeable layer and/or the at least one sensing layer comprises a silicon rubber.

8. The chemo-optical sensor unit of claim 1, wherein the first compound is present in the chemo-optical sensor unit in such a concentration that the optical response is stable when the chemo-optical sensor unit is in contact with the contact medium having a constant gas concentration.

9. The chemo-optical sensor unit of claim 1, wherein the at least one sensing layer comprises luminescent material, and wherein the at least one gas-permeable layer is adapted to prevent light from passing through the at least one gas-permeable layer.

10. The chemo-optical sensor unit of claim 1, wherein:
    the chemo-optical sensor unit is a transcutaneous sensor unit for measuring blood gas concentration; and
    the blood gas concentration corresponds to a gas concentration of $O_2$ and/or a gas concentration of $CO_2$.

11. The chemo-optical sensor unit of claim 1, further comprising:
    at least one light source adapted to irradiate the at least one sensing layer; and
    a light guiding structure connected to the at least one light source, wherein the light guiding structure is connected to the at least one photosensitive detector, and wherein at least one of: the at least one light source, the light guiding structure, and the at least one photosensitive detector are detachably connected to the chemo-optical sensor unit.

12. A system for patient monitoring and/or ventilation of a patient, comprising:
    a chemo-optical sensor unit comprising:
        at least one sensing layer adapted to be irradiated with a predetermined radiation;
        at least one gas-permeable layer adjacent to one side of the at least one sensing layer and adapted to pass gas whose concentration is to be measured through the at least one gas-permeable layer towards the at least one sensing layer;
        a contact medium configured to contact skin and, when the contact medium is in contact with the skin, is positioned between the at least one gas-permeable layer and the skin, wherein the contact medium comprises a first compound other than water, wherein the first compound is an organic compound, and wherein the chemo-optical sensor is characterized in that the at least one gas-permeable layer and the at least one sensing layer are permeable to the first compound; and
        at least one photosensitive detector adapted to measure an optical response of the at least one sensing layer to the predetermined radiation, wherein the optical response depends on the concentration of the gas; and
    at least one of a ventilation device and a monitoring device.

13. A method for conditioning a chemo-optical sensor unit for transcutaneous measurement of a concentration of a gas, comprising:
- causing a contact medium to contact skin of a patient using at least one gas-permeable layer of the chemo-optical sensor unit, wherein the contact medium is configured to be positioned between the at least one gas-permeable layer and the skin when the contact medium is in contact with the skin;
- irradiating at least one sensing layer of the chemo-optical sensor with a predetermined radiation;
- measuring a concentration of a gas that passes through the at least one gas-permeable layer of the chemo-optical sensor unit adjacent to one side of the at least one sensing layer towards the at least one sensing layer, wherein the concentration is to be measured through the at least one gas-permeable layer, wherein the contact medium comprises a first compound other than water, and wherein the at least one gas-permeable layer and the at least one sensing layer are permeable to the first compound; and
- measuring an optical response of the at least one sensing layer to the predetermined radiation using at least one photosensitive detector, wherein the optical response depends on the concentration of the gas.

14. The method of claim 13, further comprising:
causing the chemo-optical sensor unit to contact a conditioning fluid comprising the first compound.

15. The method of claim 14, wherein contacting comprising:
removing the chemo-optical sensor unit from contact with the conditioning fluid in response to determining that the first compound reached an equilibrium in at least one of: the at least one gas-permeable layer and the at least one sensing layer.

16. The method of claim 13, further comprising:
providing the chemo-optical sensor unit in a conditioning fluid comprising the first compound, wherein the conditioning fluid is chemically identical to the contact medium.

\* \* \* \* \*